United States Patent [19]
Crawford et al.

[11] Patent Number: 5,455,173
[45] Date of Patent: Oct. 3, 1995

[54] BIOLOGICAL ISOLATES FOR DEGRADING NITROAROMATICS AND NITRAMINES IN WATER AND SOILS

[75] Inventors: Ronald L. Crawford; Donald L. Crawford; Stephen B. Funk; Lisa J. Pumfrey; Karl M. Regan, all of Moscow, Id.

[73] Assignee: Idaho Research Foundation, Inc., Moscow, Id.

[21] Appl. No.: 229,413

[22] Filed: Apr. 18, 1994

Related U.S. Application Data

[63] Continuation-in-part of Ser. No. 96,735, Jul. 23, 1993, Pat. No. 5,387,271, which is a continuation-in-part of Ser. No. 508,056, Apr. 11, 1990, abandoned.

[51] Int. Cl.⁶ .................................................. D06M 16/00
[52] U.S. Cl. ................................. 435/264; 71/6; 71/903; 435/262; 435/262.5; 210/610; 210/611
[58] Field of Search .................................. 71/6, 7, 8–10, 71/903, 904; 435/262, 262.5, 264; 210/610, 611

[56] References Cited

U.S. PATENT DOCUMENTS

| | | | |
|---|---|---|---|
| 4,826,601 | 5/1989 | Spratt et al. | 210/610 |
| 4,919,813 | 4/1990 | Weaver | 210/603 |
| 4,925,552 | 5/1990 | Bateson et al. | 192/81 C |
| 4,968,427 | 11/1990 | Glanser et al. | 210/610 |
| 5,062,956 | 11/1991 | Lupton et al. | 210/611 |
| 5,071,755 | 12/1991 | Nelson et al. | 435/167 |

FOREIGN PATENT DOCUMENTS

| | | |
|---|---|---|
| 0251320A2 | 1/1988 | European Pat. Off. |
| 3818398A1 | 12/1989 | Germany. |
| 8602985 | 6/1988 | Netherlands. |

OTHER PUBLICATIONS

Goszcynski et al., "Isotopically Labelled Compounds for Hazardous Waste Site Cleanup Investigations: Part I. Synthesis of [phenyl–u–$^{14}$C] labelled 2,4–dinitro–6–sec–butylphenol (dinoseb) and [phenyl–U–$^{14}$C] labelled 4–n–propylphenol, " *J. Labelled Compounds and Radiopharmaceuticals* XXIX:35–42 (1991).

Stevens et al., "Selection and Isolation of Bacteria Capable of Degrading Dinoseb (2–sec–butyl–4,6–dinitrophenol), " *Biodegradation* 2:1–13 (1991).

Kaake et al., "Bioremediation of Soils Contaminated with the Herbicide 2–sec–Butyl–4,6–Dinitrophenol (Dinoseb), " *Appl. Env. Microbiol.* 58:1683–1689 (1992).

Stevens et al., "Biodegradation of Dinoseb (2–sec–Butyl–4, 6–Dinitrophenol) in Several Idaho Soils with Various Dinoseb Exposure Histories, " *Appl. Env. Microbio.* 56:133–139 (1990).

(List continued on next page.)

*Primary Examiner*—Ferris Lander
*Attorney, Agent, or Firm*—Klarquist Sparkman Campbell Leigh & Whinston

[57] ABSTRACT

Three individual strains of anaerobic microorganisms are disclosed. Each has an ability to degrade nitroaromatic and nitramine compounds under anaerobic conditions. The strains, identified as LJP-1, SBF-1, and KMR-1, appear to be of Clostridium bifermentans. The strains were isolated from consortia of anaerobic microorganisms grown in a chemostat in which the "munitions" compounds TNT (as a representative nitroaromatic) and "RDX" nad "HMX" (as representative nitramines) were administered as sole sources of carbon for the microorganisms. The isolated strains, either individually or as mixtures thereof, can be used in methods for degrading, under anaerobic conditions (i.e., redox potential <–200 mV), a contaminant nitroaromatic and/or nitramine compound in water or soil (as an aqueous slurry, i.e., "fluid medium"). The strains will degrade nitroaromatics and nitramines in such fluid media either alone or with other microorganisms present in the fluid medium.

13 Claims, 7 Drawing Sheets

OTHER PUBLICATIONS

Tiedje and Stevens, "The Ecology of an Anerobic Dechlorinating Consortium, " in Omenn (ed.) *Environmental Biotechnology* pp. 3–14 (1988).

Hallas et al., "Microbial Transformation of Nitroaromatic Compounds in Sewage Effluent, " *Appl. Environ Microbiol.* 45:1234–1241 (1983).

Channon et al., "The Metabolism of 2:4:6–Trinitrotuluene (α–T.N.T.), " *Biochem. J.* 38:70–85 (1994).

Zeyer et al., "Degradation of o–Nitrophenol and m–Nitrophenol by a *Pseudomonas putida,* " *J. Agric. Food Chem.* 32:238–242 (1984).

Simmons et al., "Oxidative Co–Oligomerization of Guaiacol and 4–Chloroaniline, " *Environ. Sci. Techol.* 23:115–121 (1989).

Cartwright et al., "Bacterial Degradation of the Nitrobenzoic Acids, " *Biochem. J.* 71:248–261 (1958).

Kaplan, "Biotransformation Pathways of Hazardous Energetic Organo–Nitro Compounds, " in Kamely, D. et al. (eds.), *Biotechnology and Biodegradation,* Gulf Pub. Co., pp. 155–180 (1990).

Gottschalk, *Bacterial Metabolism* (2d ed)., Springer Verlag, NY, pp. 157–162 (1986).

Naulmova et al., "Possibility of Deep Bacterial Destruction of 2,4,6–Trinitrotoluene, " *Mikrobiologiya* 57:218–222 (1988).

Schink, "Principles and Limits of Anaerobic Degradation: Environmental and Technological Aspects, " in Zinder (ed.), *Biology of Anaerobic Microoranisms,* Wiley, N.Y., pp. 771–846 (1988).

McCormick et al., "Microbial Transformation of 2,4,6–Trinitrotoluene and Other Nitroaromatic Compounds, " *Appl. Environ. Microbiol.* 31:949–958 (1976).

Tschech et al., "Methanogenic Degradation of Anthranilate (2–Aminobenzoate), " *System. Appl. Microbiol.* 11:9–12 (1988).

Doyle et al., "Effect of Dairy Manure and Sewage Sludge on [14–C]–Pesticide Degradation in Soil, " *J. Agric. Food Chem.* 26:987–989 (1978).

Spain et al., "Enzymatic Oxidation of p–Nitrophenol, " *Biochem. and Biophys. Research Communications* 88:634–641 (1979).

Jensen et al., "Microorganisms that Decompose Nitro–Aromatic Compounds, With Special Reference to Dinitro–Ortho–Cresol, " *Acta Agriculturae Scandinavica* 17:115–126 (1967).

Berry et al., "Microbial Metabolism of Homocyclic and Heterocyclic Aromatic Compounds Under Anaerobic Conditions, " *Microbiol. Rev.* 51:43–59 (1987).

Parris, "Environmental and Metabolic Transformations of Primary Aromatic Amines and Related Compounds, " *Residue Reviews* 76:1–30 (1980).

Wallnöfer et al., "Transformation of Dinitrophenol–Herbicides by Azotobacter Sp., " *Chemosphere* 12:967–972 (1978).

Ziegler et al., "Activation of Aromatic Acids and Aerobic 2–Aminobenzoate Metabolism in a Denitrifying *Pseudomonas* Strain, " *Arch. Microbiol.* 151:171–176 (1989).

Ziegler et al., "Studies on the Anaerobic Degradation of Benzoic Acid and 2–Aminobenzoic Acid by a Denitrifying *Pseudomonas* Strain, " *Arch. Microbiol.* 149:62–69 (1987).

Smolenski et al., "Biodegradation of Cresol Isomers in Anoxic Aquifers, " *Appl. Environ. Microbiol.* 53:710–716 (1987).

Kuhn et al., "Anaerobic Degradation of Alkylated Benzenes in Denitrifying Laboratory Aquifer Columns, " *Appl. Environ. Microbiol.* 54:490–496 (1988).

Frööslie et al., "Ruminal Metabolism of DNOC and DNBP. " *Acta Vet. Scand.* 11:114–132 (1970).

Tratnyek et al., "Abiotic Reduction of Nitro Aromatic Pesticides in Anaerobic Laboratory Systems, " *J. Agric. Food Chem.* 37:248–254 (1989).

Vlassak et al., "Dinoseb as a Specific Inhibitor of Nitrogen Fixation in Soil, " *Soil Biol. Biochem.* 8:91–93 (1976).

Federle, "Mineralization of Monosubstituted Aromatic Compounds in Unsaturated and Saturated Subsurface Soils. " *Can. J. Microbiol.* 34:1037–1042 (1988).

Braun et al., "Anaerobic Degradation of 2–Aminobenzoate (Anthranilic Acid) by Denitrifying Bacteria, " *Appl. Environ. Microbiol.* 48:102–107 (1984).

Kaplan et al., "Thermophilic Biotransformations of 2,4,6–Trinitrotoluene Under Simulated Composting Conditions, " *Appl. Environ. Microbiol.* 44:757–760 (1982).

Stevens, "Biodegradation of Dinoseb (2–sec–Butyl–4,6–Dinitrophenol) and Bioremediation of Dinoseb–Contaminated Soils, " Ph.D. Thesis, University of Idaho (1989).

BIOLOGICAL ISOLATES FOR DEGRADING NITROAROMATICS AND NITRAMINES IN WATER AND SOILS

CROSS REFERENCE TO RELATED APPLICATION

This application is a continuation-in-part of U.S. patent application Ser. No. 08/096,735 (incorporated herein by reference), filed on Jul. 23, 1993, now U.S. Pat. No. 5,787,271, Feb. 7, 1995, which is a file-wrapper continuation-in-part of U.S. patent application Ser. No. 07/508,056, filed on Apr. 11, 1990, now abandoned.

ACKNOWLEDGEMENT

Research leading to this invention was federally supported by grant nos. F49620-93-1-0464 and ASOSR 91-0315 from the U.S. Department of Defense/Air Force, and by grant no. CR820804 from the Environmental Protection Agency. The government has certain rights in this invention.

FIELD OF THE INVENTION

This invention relates to microorganism isolates capable of biodegrading nitroaromatic and nitramine compounds in water and soils.

BACKGROUND OF THE INVENTION

A number of nitroaromatic compounds have substantial toxicity. In fact, certain of such compounds have been effectively used as herbicides (e.g., "dinoseb" (2-(1-methylpropyl)-4,6-dinitrophenol)), insecticides, and miticides. Perhaps the most notorious use of certain of these compounds is as explosives, such as 2,4,6-trinitrotoluene ("TNT"), dinitrotoluene ("DNT"), and picric acid (2,4,6-trinitrophenol). A similar group of compounds consists of the nitramines, exemplified by the "munitions" explosives hexahydro-1,3,5-triazine ("RDX") and octahydro-1,3,5,7-tetranitro-1,3,5,7-tetraazocine ("HMX"). Contaminant nitroaromatics and nitramines are generally persistent in natural environments, where the residual toxicity of these compounds can present a substantial hazard. A number of sites worldwide are contaminated with one or more of these compounds, including both manufacturing and military sites, thereby rendering the sites unfit for other uses. Thus, there is a need for ways in which such sites can be remediated for other uses.

Heretofore, land farming has generally been employed in attempts to remove these chemicals from contaminated lands, wherein, for example, contaminated soil is augmented with fertilizer and the mixture aerated to promote microbial activity. Unfortunately, nitroaromatics and nitramines are not satisfactorily degraded by land farming or other aerobic methods. Possible reasons include lack of indigenous nitroaromatic-degrading microorganisms, partitioning of the contaminant chemicals to biologically sequestered or inhospitable parts of the environment, and accumulation of toxic partial-breakdown by-products. Problems with land farming in general include the slow rate of biodegradation, high expense, and accumulation of toxic by-products.

Other methods to remove nitroaromatics and nitramines from contaminated soils have also met with little practical success. Such methods include transportation of contaminated soil to hazardous waste dumps, and on-site incineration of the soil. Problems with such methods include high cost and poor accountability of the responsible party.

Certain nitroaromatic molecules, and possibly certain nitramines, are susceptible to "transformation" reactions in natural environments. "Transformation" (or "biotransformation" if biologically mediated) is not the same as "biodegradation." As a result of transformation, molecules of the contaminant compound are converted into other environmentally resistant compounds that retain a substantial amount of the residual toxicity of the original compound. These other compounds can have larger molecular weights than the original contaminant compounds. "Biodegradation" means the biologically mediated conversion of the contaminant compound at least to organic acids and/or other simple organic molecules that lack the residual toxicity of the original compound and that are readily metabolized by other organisms. "Mineralization" is degradation carried to the extreme, in which molecules of the contaminant compound are converted to carbon dioxide and other non-organic fundamental compounds.

For example, the anaerobic bacteria Veillonella alkalescens can reductively transform nitroaromatic compounds, converting the nitro groups to amino groups. McCormack et al., Appl. Environ. Microbiol. 31:949–958 (1976). Unfortunately, aminoaromatic derivatives of nitroaromatics tend to be transformed in the presence of atmospheric oxygen to polymeric (large molecular weight) compounds, Parris, Residue Revs. 76:1–30 (1980), that are usually incorporated in the field into long-lived soil humic matter that retains a substantial amount of the toxicity of the original compound. Channon et al., Biochem. J. 38:70–85 (1944); McCormick et al., Appl. Environ. Microbiol. 31:949–958 (1976); Simmons et al., Environ. Sci. Technol. 23:115–121 (1989).

Biodegradation of a nitroaromatic compound by a microorganism would require that the microorganism be capable of removing nitro groups and cleaving aromatic rings to alkyl groups. Biodegradation of a nitramine compound would also require an ability of the responsible microorganism to remove nitro groups. No single anaerobic strain capable of carrying out this process has been isolated to date.

In co-pending U.S. Patent application serial no. 08/096,735, incorporated herein by reference, a biological system for degrading contaminant nitroaromatics in waters and soils is disclosed. The method typically involves an aerobic stage followed by an anaerobic stage, wherein the aerobic stage is short-lived to prevent formation of recalcitrant aminoaromatic polymers from the nitroaromatics. Actual degradation, and even mineralization, of the nitroaromatic occurs during the anaerobic stage, involving multiple reactions performed by microorganisms comprising an anaerobic consortium. The consortium is preferably obtained by removing a sample of soil from the contaminated site and culturing the resident microorganisms under anaerobic conditions in the presence of the particular nitroaromatic(s) to be degraded. Over time in such conditions, the culture becomes enriched in microorganisms capable of degrading the target nitroaromatic(s). The resulting enriched culture can then be used to inoculate a quantity of soil or water to be bioremediated. Even though this method has substantial utility, it would be desirable to have various pure cultures of microorganisms each capable of completely mineralizing one or more specific nitroaromatic and/or nitramine compounds.

Thus, there remains a need for pure cultures of microorganisms capable of at least biodegrading nitroaromatics and/or nitramines, and for methods for biodegrading such compounds in which a pure culture of microorganisms can be added to contaminated soil or water for the purpose of biodegrading such compounds present as contaminants in the soil or water.

Further, there is a need for such a method that can be performed at a natural site that has soil or water contaminated with a nitroaromatic and/or nitramine compound.

SUMMARY OF THE INVENTION

The foregoing needs are met by various aspects of the present invention. According to one aspect of the present invention, three isolated strains of anaerobic bacteria are provided, strains LJP-1, SBF-1, and KMR-1, that exhibit an ability to degrade nitroaromatic and nitramine compounds. Evaluation of the three strains indicates that they are of the species Clebsiella bifermentans. These strains have been deposited with the American Type Culture Collection (ATCC); thus, the claimed strains have the identifying characteristics, as disclosed herein, of ATCC accession numbers ATCC 55559, ATCC 55561, and ATCC 55560, respectively.

All three strains exhibit an ability to degrade, by way of example, TNT, RMX, and HMX to organic acids. Because TNT (a representative nitroaromatic) and RDX and HMX (representative nitramines) present chemical structures and moieties that are characteristic of their respective groups of compounds, the metabolic chemistry applied by any of the isolated strains to degrading any of various nitroaromatics and nitramines would be substantially the same as applied to TNT, RDX, and HMX. For example, degrading a nitroaromatic would require removal of the nitro groups and cleavage of the aromatic ring(s). The fact that the isolated strains can rapidly degrade TNT indicates that the strains would be capable of degrading any of various other nitroaromatics. Similarly, degrading a nitramine would require removal of the nitro groups and cleavage of the alkylamino backbone of the molecule. The fact that the isolated strains can efficiently degrade RDX and HMX indicates that the strains would be capable of degrading any of various other nitramines.

Any of the three strains, or a mixture thereof, can be added as an anaerobic inoculum to a fluid medium comprising water or water and soil contaminated with one or more nitroaromatics and/or nitramines. The fluid medium is as described in detail in U.S. patent Ser. No. 08/096,735, incorporated herein by reference. This reference also sets forth in detail various methods for degrading nitroaromatics in soil or water in which an anaerobic consortium of microorganisms is added to the fluid medium. According to the present invention, any of the three isolated strains, or a mixture thereof, can be used in place of, or as an augmentation to, the anaerobic consortium in such methods. Since the strains according to the present invention are capable of degrading nitroaromatics and nitramines, the strains can be used as the only source of anaerobic microorganisms used for degrading contaminant nitroaromatics and/or nitramines in the water or soil under anaerobic conditions.

In methods employing any of the isolated strains disclosed herein for degrading contaminant nitroaromatics and/or nitramines in soil, the soil is made into a "fluid medium" by addition of a sufficient amount of an aqueous liquid to form a slurry. The fluid medium (soil slurry or water) is made anaerobic (redox potential about −200 mV or less) by any of various suitable methods including, but not limited to, preheating to drive off oxygen; addition of a reductant (oxygen scavenging agent); adding sugar or starch to the fluid medium and performing an initial aerobic fermentation of the sugar or starch in the fluid medium using an inoculum of fermentative aerobic microorganisms so as to depress the redox potential of the medium; and passing a gas not containing oxygen through the fluid medium.

BRIEF DESCRIPTION OF THE DRAWING

The drawing consists of multiple figures, in which.

DETAILED DESCRIPTION

I. General Procedures

Figure 1:
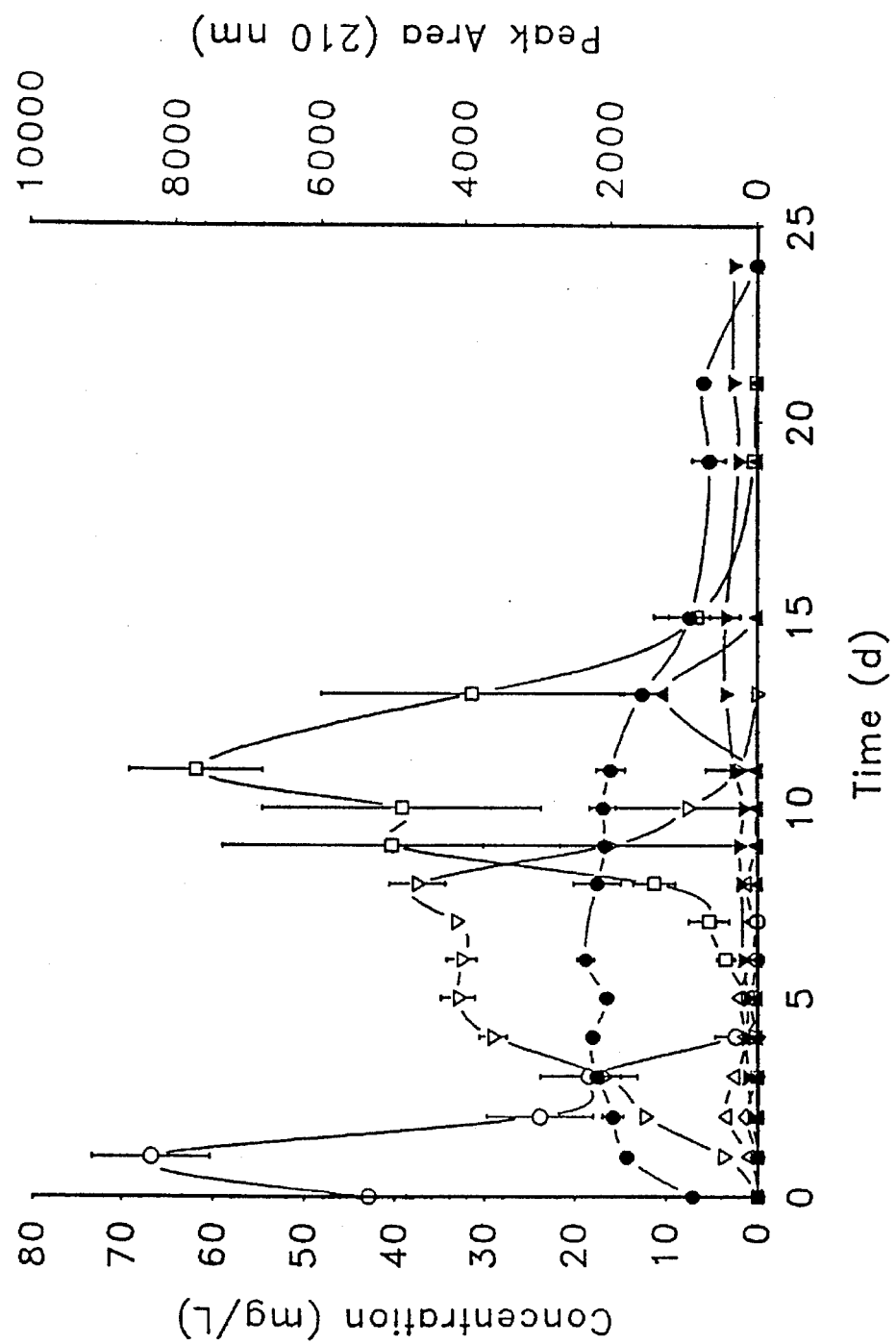
FIG. 1 is a plot showing degradation of TNT (open circles) by an anaerobic consortium of microorganisms used as a source of the SBF-1 strain according to the present invention; other symbols represent the production and subsequent disappearance of various compounds resulting from TNT degradation by the consortium; error bars represent one standard deviation (n=3).

The terms "biodegradation," "biotransformation," and "mineralization" are defined above. "Bioremediation" is any of various processes, employing living organisms (usually, but not necessarily, microorganisms), resulting in substantial removal of a subject toxic compound from a soil or water. Microorganism strains, and biodegradation methods as described herein employing such strains, can be used to bioremediate a soil or water.

Microorganisms capable of degrading a nitroaromatic or nitramine compound can be preliminarily selected and enriched using a chemostat as described in U.S. Pat. No. 08/096,735, incorporated herein by reference. In a typical use of such a chemostat, glass beads are placed in the bottom of the chemostat vessel to act as a soil-holding matrix. As a result, both aerated (supernatant liquid) and non-aerated (sediment) enrichment conditions can be simultaneously maintained in the chemostat.

To provide a source of mineral nutrients to the microorganisms in the chemostat, a mineral nutrient solution can be used that contains the following solutes: $KH_2PO_4$ (272 mg/L), $K_2HPO_4$ (348 mg/L), $Na_2SO_4$ (5 mg/L), $MgSO_4 \cdot 7H_2O$ (5 mg/L), $CaCl_2 \cdot 2H_2O$ (1 mg/L), and $FeSO_4$ (0.5 mg/L). The nutrient solution can be supplemented with selected carbon and nitrogen sources, as discussed further below, so as to provide a selection pressure suitable for enriching the biological population in the chemostat for microorganisms capable of degrading the subject nitroaromatic or nitramine compound.

When beginning a selection protocol for new nitroaromatic- or nitramine-degrading microorganism, the chemostat is typically inoculated with an initial population of microorganisms such as microorganisms indigenous to the soil found at a nitroaromatic- or nitramine-contaminated site. The initial inoculum can also be obtained from soil or water that had been contaminated with a nitroaromatic and/or nitramine and subsequently bioremediated. The initial inoculum can be supplemented (if desired or indicated) by a sewage sludge inoculum, representing an unusually rich and genetically diverse source of microorganisms.

The chemostat is employed for producing a consortium of microorganisms capable of utilizing one or more particular nitroaromatics and/or nitramines ("contaminant compound") as a sole source of carbon. A "selection pressure" is applied to the population of microorganisms in the chemostat by adding the contaminant compound to the chemostat at an initially small dose (normally along with other more conventional carbon source(s) such as a sugar), then progressively increasing the dose of the contaminant compound over time (normally while slowly withdrawing the other carbon sources). Eventually, the microorganisms in the chemostat become adapted to utilize the contaminant compound as a carbon source without a need for other carbon sources. Thus, over time, the microorganisms develop an ability to degrade the contaminant compound.

The culture in the chemostat can be maintained indefinitely, and the selection pressure can be applied over a long time, including years, if desired.

After the microorganisms in the chemostat develop an ability to degrade the contaminant compound as described above, samples of liquid are removed from the chemostat and plated on nutrient agar to obtain isolates of specific microorganisms. The isolates can be cultured under aerobic, anaerobic, or microaerophilic conditions in which each isolate's individual abilities to transform or degrade a nitroaromatic or nitramine can be evaluated. For aerobic culturing, the mineral nutrient solution described above can be used, supplemented with one or more of the following as required: subject nitroaromatic or nitramine (usually 10 to 100 mg/L), glucose or fructose (500 mg/L), $NH_4Cl$ (1.0 g/L), $MnCl_2 \cdot 4H_2O$ (0.5 mg/L), $H_3BO_3$ (0.05 mg/L), $ZnCl_2$ (0.05 mg/L), $CuCl_2$ (0.03 mg/L), $Na_2MoO_4 \cdot 2H_2O$ (0.01 mg/L), $CoCl_1 \cdot 6H_2O$ (0.5 mg/L), $NiCl_2 \cdot 6H_2O$ (0.05 mg/L), $Na_2SeO_3$ (0.05 mg/L), and a vitamin solution as recommended by Wolin et al., J. Biol. Chem. 238:2882–2886 (1963). Yeast extract can also be added to the culture solution to a concentration of 0.5 g/L. (Yeast extract serves as a convenient source of additional carbon and energy for the isolates, as well as a source of additional vitamins and cofactors.)

Culturing an isolate under denitrifying conditions provides a way in which to select for facultative anaerobes. Under such conditions, nitrate is employed by respiring microorganisms as an electron acceptor rather than oxygen as used by respiring aerobic microorganisms. (Facultative anaerobes can be cultured in either aerobic or anaerobic environments.) For example, preparing a medium for culturing isolates under denitrifying (anaerobic) conditions can be performed by supplementing the aerobic culture medium with 1 g/L $KNO_3$, boiling the medium under nitrogen gas, then sealing the medium in glass containers with butyl rubber stoppers before inoculation with the isolate.

A reduced anaerobic mineral medium (RAMM) can be used for culturing isolates under anaerobic conditions. RAMM comprises the same ingredients as listed above for aerobic cultures, but supplemented with 10 mg/L resazurin (as a redox indicator), 10 mg/L $NaS_2O_4 \cdot 2H_2O$ (as a reducing agent), and 1.2 g/L $NaHCO_3$. (Preferably, 0.1 g/L yeast extract is also added.)

Anaerobic cultures can be grown in serum bottles or batch tubes sealed with butyl rubber stoppers, using strict anaerobic procedures, as detailed in Ljungdahl and Wiegel, "Working with Anaerobic Bacteria," in Demain and Solomon (eds.), Manual of Industrial Microbiology and Biotechnology, American Society for Microbiology, Washington, D.C. (1986) pp. 84–96.

To quantify the transformation of a subject nitroaromatic or nitramine compound, concentrations of the subject compound can be assayed in the medium by High Performance Liquid Chromatography (HPLC) or other suitable analytical method. With an HPLC instrument, detection of the subject compound and its transformation and degradation products can be performed using a diode-array detector, measuring UV absorption at selected absorption maxima and or continuous scanning over a suitable wavelength range.

A "consortium" (i.e., a stable mixed population) of anaerobic microorganisms capable of degrading the subject nitroaromatic or nitramine compound can be enriched from the population of such organisms in the chemostat as follows: Sediment from the chemostat as described above is used to inoculate strictly anaerobic medium comprised of the mineral nutrient solution described above with added 1 g/L fructose, 1 g/L $NH_4Cl$, and 100 ppm of the subject compound. After incubating for a time (usually several weeks), the subject compound in the culture decreases in concentration often with a corresponding increase in one or more by-products (such as acetate). Turbidity of the medium usually accompanies the foregoing change in chemical profile, indicating growth of the microorganisms. Sediment-free anaerobic nitroaromatic- or nitramine-degrading cultures can be maintained indefinitely by, for example, making three transfers in mineral medium, followed by one transfer in yeast extract-containing medium, followed by further mineral medium transfers. After eighteen months of such transfers, the cultures are generally observed to remain stable in the yeast-extract containing medium.

Degradation of the subject nitroaromatic or nitramine by the anaerobic microorganisms, including by the anaerobic consortium, does not occur unless strict anaerobic procedures are followed during preparation of the media and during culture transfers.

Important parameters to be controlled for optimal degradation of nitroaromatics and nitramines include temperature, nitrogen concentration, and pH. A general temperature range is from about 15 to about 37° C. (preferably 20 to 30° C.); and a general pH range is from 6 to 8 (preferably 6.5 to 7).

General procedures for degrading nitroaromatic compounds comprising an aerobic fermentation stage followed by an anaerobic stage are set forth in U.S. patent application Ser. No. 08/096,735, incorporated herein by reference.

II. Bioremediation of Munitions-Contaminated Soil Using an Anaerobic Consortium of Microorganisms.

In the experiments described herein, bioremediation of a sample of a nitroaromatic- and nitramine-contaminated soil from an army munitions depot was demonstrated. The soil contained 12,000 mg/kg trinitrotoluene ("TNT"; a representative nitroaromatic), 3,000 mg/kg hexahydro-1,3,5-triazine (abbreviated "RDX"; a first representative nitramine), and 30 mg/kg octahydro-1,3,5,7-tetranitro-1,3,5,7-tetraazocine (abbreviated "HMX"; a second representative nitramine). A consortium of anaerobic bacteria produced as described generally above was used to degrade these contaminants to non-toxic, non-aromatic mineralizable end-products.

A population of anaerobic microorganisms was produced in a chemostat using general procedures as described above. The chemostat was initially inoculated with microorganisms obtained from a dinoseb- and TNT-contaminated soil and with sewage sludge. Over time, "munitions compounds": TNT, RMX, and HMX, were added to the chemostat in upwardly ramped dosages. Thus, the microorganism culture in the chemostat, comprising a consortium of anaerobic microorganisms, adapted over time to utilize the munitions compounds as sole carbon sources. During this adaptation period, the microorganisms in the bioreactor underwent several sequential stages of adaptation, characterized by the accumulation of specific metabolites of the munitions compounds as identified by HPLC, GC/MS, and $^{14}$C-radiolabeled tracer studies.

A sample of the microorganism consortium from the chemostat was incubated, in triplicate cultures (each receiving 4 g of the consortium), with 4 grams of the contaminated soil, 400 mL of 50 mM phosphate buffer (pH 7), 25 mM ammonium chloride, and 4 g of potato processing by-product (starch). Each culture in the triplicate was contained in a 500-mL Erlenmeyer wide mouth flask covered with aluminum foil. Incubation was at 30° C. in the dark. Samples of the aqueous phase and soil extractions of each culture were analyzed by HPLC. The microorganisms were observed to completely remove TNT from the culture in 5 days and RDX from the culture in 24 days. Degradation of the TNT was observed to progress to reduced aminonitro compounds, then paracresols, then to other compounds (FIG. 1). Non-aromatic volatile organic acids such as acetate were also observed as products of TNT degradation by the cultures.

In FIG. 1, data points represent averages of triplicate analyses. Concentrations of known compounds were determined by comparison of peak areas to those of authentic standards, wherein open circles represent TNT, closed circles represent RDX, open downward-pointing triangles represent 4A26DNT (4-amino-2,6-dinitrotoluene), open squares represent 24DA6NT (2,4-diamino-6-nitrotoluene), open diamonds represent an uncharacterized intermediate "A," open upward-pointing triangles represent a second uncharacterized intermediate "B," closed downward-pointing triangles represent a third uncharacterized intermediate "D," and closed upward-pointing triangles represent a fourth uncharacterized intermediate "E." Error bars represent one standard deviation (n=3).

Different enzyme systems are believed to be involved in the degradation of nitroaromatics and nitramines by the microorganisms in the consortium. Normally, TNT and other nitroaromatics are more resistant to degradation than nitramines such as RDX; the cultures investigated above, in contrast, appeared to attack TNT before the nitramines. Thus, some form of co-metabolite repression may be occurring in the cultures, wherein the TNT substrate is preferred over a nitramine substrate.

Figure 2:
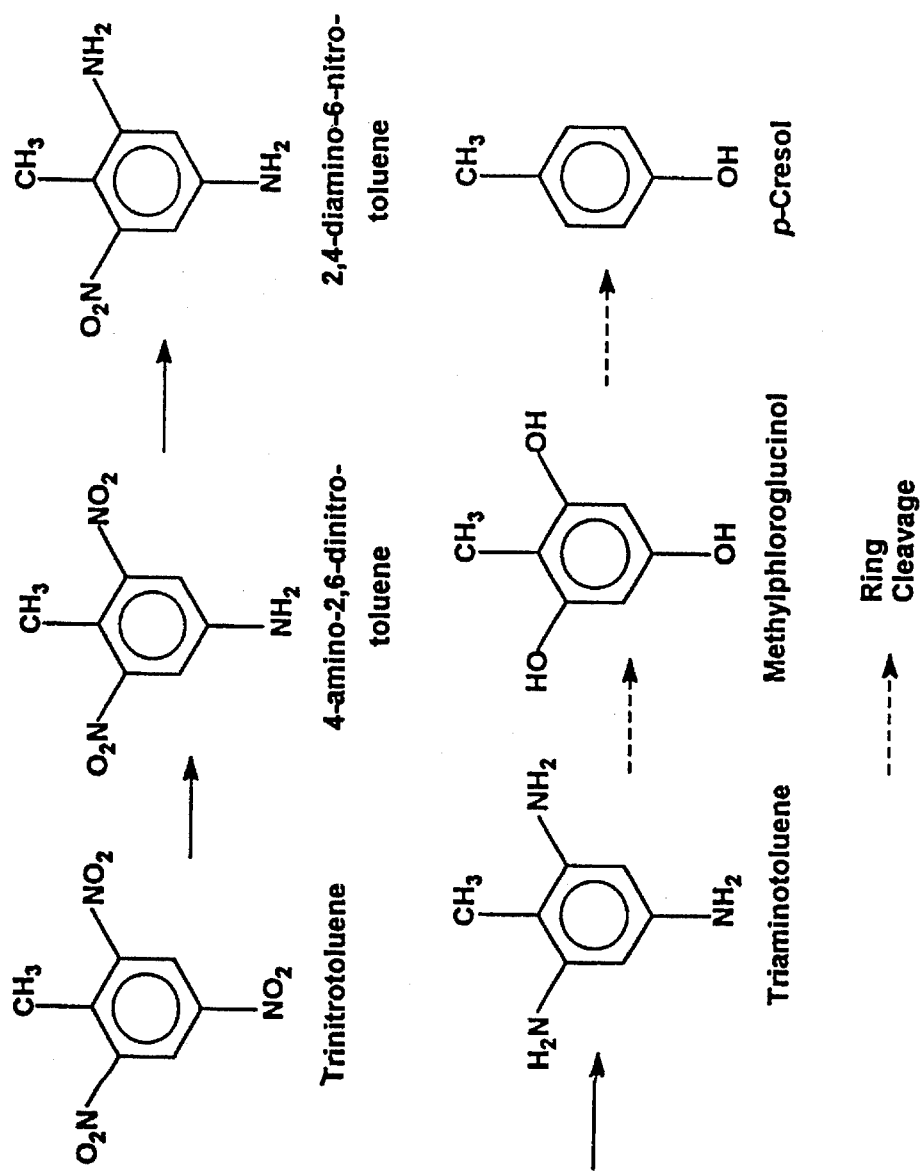
FIG. 2 shows a representative pathway by which the consortium of FIG. 1 degrades TNT to p-cresol, based upon the results of FIG. 1 and other experiments.

The first TNT metabolites to accumulate in culture supernatants were the reduced TNT intermediates 4A26DNT and 24DA6NT. A second stage of adaptation led to the disappearance of these reduced intermediates and the accumulation of methylphloroglucinol (2,4,6-trihydroxytoluene). In a third stage of adaptation, the trihydroxytoluene gave way to p-cresol (4-methylphenol). These metabolic steps are illustrated in FIG. 2.

Cultures obtained from the chemostat after three years of acclimatization to TNT as a sole carbon source were observed to produce detectable amounts of p-cresol from TNT (125 mg/L) in 14 days.

In another experiment, a TNT- and RDX-contaminated soil was flooded with 50 mM phosphate buffer (pH 7). Starch was added as a supplemental carbon substrate. An inoculum of strict anaerobes from the chemostat, as described above, was added and the resulting mixture was incubated (temperature range 20 to 37° C.) under static and strictly anaerobic conditions. Removal of TNT molecules from these cultures occurred within 4 days. Reduced intermediates that were generated from the degradation of the TNT and RDX disappeared from the mixture within 24 days. This result was achieved over a range of temperature of 20 to 37° C., and was improved further upon addition of 25 mM ammonium ion to cultures buffered with 50 mM potassium phosphate. The optimum pH was 6.5 to 7.0.

III. Isolation of a First Strain (SBF-1) of Bacterium Capable of Degrading TNT and Nitramines.

A 400-μL sample was removed from the chemostat culture described in II, above, and streaked onto anaerobic nutrient agar. Three colony types were observed to grow on the plates after overnight incubation under strict anaerobic conditions at 30° C. Representative colonies of all three types were picked and streaked onto tripticase-soy agar (TSA) plus 15 ppm TNT. Only one of the colony types grew up overnight on this medium. This colony was the subject of further work.

The single colony described above was cultured in anaerobic tripticase-soy broth (TSB) plus 50 ppm TNT. After three days of such culturing, no detectable TNT or known intermediates were evident in the culture medium, as determined by HPLC. Light microscopy of the microorganism revealed a long, thin rod morphology (about 15 μm×1 μm). According to results of the commercially available API AN-IDENT test, the bacterium was identified as a strain of Clostridium bifermentans. The strain designated "SBF-1" has been deposited with the American Type Culture Collection (ATCC) under accession number ATCC 55561.

IV. Isolation of a Second Strain (LJP-1) of Bacterium Capable of Degrading TNT

A pure bacterial culture capable of degrading TNT to carbon dioxide and organic acids was isolated using an anaerobic, methanogenic bench-top bioreactor (chemostat) as described above. The initial inoculum of microorganisms in the chemostat was obtained from a soil obtained from a munitions site previously contaminated with the nitroaromatic "dinoseb" and from a sewage sludge. Thus, the bioreactor was initially inoculated with an anaerobic consortium of microorganisms lacking an ability to degrade TNT.

Over a period of 13 months, the liquid medium in the chemostat was supplemented with TNT, RMX, and HMX as sole sources of carbon. The medium also included essential nutrients as listed above. During the 13-month period of progressive exposure to TNT, RMX, and HMX, the anaerobic consortium in the reactor evolved an ability to degrade TNT. During this evolution, the culture passed through a number of sequential stages of adaptation each characterized by the accumulation in the medium of specific TNT metabolites, which were identified by HPLC, GC/MS, and $^{14}$C-radiolabeled tracer studies. The first metabolites to accumulate were reduced intermediates of TNT such as 4-amino-2,6-nitrotoluene (4A26NT) and 2,4-diamino-6-nitrotoluene (24DA6NT). A second stage of adaptation led to the disappearance of these intermediates and the accumulation of trihydroxytoluene. In a third stage of adaptation, trihydroxytoluene gave way to p-cresol (4-hydroxytoluene). After the 13-month period of exposure to TNT, acetate began to accumulate as the first identifiable non-aromatic TNT degradation product. The microorganism culture at this stage is termed herein the "TNT-adapted culture."

When munitions wastes containing TNT, RDX, and HMX were provided to the TNT-adapted culture under optimized conditions for growth of the TNT-degrading microorganisms (final TNT concentration 125 mg/kg) detectable amounts of p-cresol accumulated in the bioreactor within 14 days.

A sample of the TNT-adapted culture was removed from the bioreactor. In an anaerobic glove box used to maintain strict anaerobic conditions, isolation of specific microorganisms from the sample was begun by serially diluting the sample and plating the dilutions onto plates of Trypticase Soy Agar (TSA) supplemented with 5% (w/v) of Yeast Extract. The TSA medium also contained 20 mg/L of TNT. Following incubation, isolated colonies were picked and restreaked on the same medium. Twelve isolates were obtained.

Each isolate was grown anaerobically in a minimal mineral salts medium containing 20 mM phosphate, carbonate buffer at pH 7–8, with TNT (30 mg/L) as the sole source of carbon and nitrogen for growth. The cultures were observed for growth (viable counts), and monitored for production of TNT metabolites by HPLC. One strain, termed "LJP-1" exhibited microbial growth, elimination of TNT from the medium, and production of TNT degradation intermediates. Further work was performed with this strain only.

Strain LJP-1 was examined for its ability to grow anaerobically in a TNT minimal medium (mineral salts broth containing 30 mg/L TNT). As a control, LJP-1 was inoculated into the mineral salts broth lacking TNT or any other carbon source. The LJP-1 inoculum was prepared by washing 24-hours-old cells from TSA+YE plates using mineral salts broth lacking TNT. Thirty mL of the resulting cell suspension was used to inoculate 30 mL TNT minimal medium in which the final TNT concentration was 30 mg/L. The cultures were incubated at 30° C.; samples were removed at time 0, 12 and 49 hours.

Viable plate counts were determined for the 0-, 12-, and 49-hour samples on TSA/YE agar. All three samples exhibited a 3-log increase in cell numbers per mL after 48 hours' growth in TNT minimal medium; in contrast, cell number declined from time 0 when TNT was omitted from the medium. Results are shown below in Table 1.

TABLE 1

| Incubation Time (Hr) | Viable Count Colony Forming Units (CFU)/ml | |
|---|---|---|
| | Medium − TNT × $10^6$ | Medium + TNT × $10^6$ |
| 0 | 1.0 | 1.0 |
| 12 | 0.42 | 2.8 |
| 24 | 0.008 | 900 |
| 48 | nd | 1500 | nd = not done

A Gram stain and a spore stain were performed on a young, anaerobically grown culture of LJP-1, as was a spore stain. The stained cells were examined microscopically. Also, wet mounts of the cells were examined under a light microscope. These examinations revealed the presence of large numbers of Gram positive, endospore-forming rods. Thus, LJP-1 was tentatively identified as a strain of Clostridium.

The foregoing growth experiments showed that, during anaerobic growth, LJP-1 removed TNT from the minimal growth medium and produced TNT metabolites. The cultures also indicated the production of volatile organic acids from the TNT. In light of these observations, a TNT degradation experiment was conducted using [U]-$^{14}$C-ring labeled TNT as a carbon source in the minimal medium. Serum bottles each containing 100 mL minimal medium (with 50 mg/L TNT) were inoculated with a 10% inoculum of cells, obtained from the TSA/YE plates, suspended in minimal medium containing 208,000 DPM of $^{14}$C-TNT (>98% purity). The cultures were sealed and incubated anaerobically, without shaking, at 30° C. All TNT-containing cultures were run in duplicate (termed cultures "A1" and "A2"). A single uninoculated control was also run. Samples from each culture (including controls) were removed after 1 day (24 hours), 4 days, and 7 days. Each sample was analyzed by HPLC for the presence of TNT, TNT degradation intermediates, and any volatile organic acids (VOAs). $^{14}$C present in each of the peaks eluted from the HPLC were quantified by liquid scintillation counting. Each culture was also flushed with nitrogen to recover $CO_2$ and volatile organic compounds. (Compounds in the flushed eluate were captured using a trapping train consisting of a first vial containing 10 mL BIOSAFE scintillation cocktail to trap volatile organics, then two downstream vials connected in series and each containing 10 mL BIOSAFE scintillation cocktail with 1.0 mL CARBOSORB to serve as $CO_2$ traps).

To determine whether any $^{14}$C was present in the cells, the cells were collected by filtration, washed with water, then with 10-percent trichloroacetic acid (TCA), then with 5-percent TCA, and finally with methanol. Counts remaining on the filter were deemed to be provided by the cells. Any counts present in the water and TCA solutions used for washing were also quantified. Results for the 24-hour cultures are shown in Table 2 (results after 4 and 7 days were substantially the same as the 24-hour results).

TABLE 2

| Fraction | % of $^{14}$C Recovered (DPM)[a] | | |
|---|---|---|---|
| | Uninoculated Control | Culture A1 | Culture A2 |
| $CO_2$ | 0 | 2.0 | 6.0 |
| Volatile Organics | 0 | 4.0 | 5.0 |

TABLE 2-continued

| | % of $^{14}$C Recovered (DPM)[a] | | |
|---|---|---|---|
| Fraction | Uninoculated Control | Culture A1 | Culture A2 |
| Biomass | 0 | 3.0 | 2.0 |
| Water Wash[b] | 0 | 54.0 | 50.0 |
| 10% TCA Wash[b] | 0 | 18.0 | 24.0 |
| 5% TCA Wash[b] | 0 | 9.0 | 9.0 |
| Methanol Wash[b] | 0 | 0.1 | 16.0 |
| Culture Medium | 100 | 2.0 | 2.0 |
| Total Recoveries | 100 | 101.1 | 104.0 |

[a]The total DPM per culture were 208,000
[b]These represent counts recovered upon washing the cells present on the filter. Since the extraction procedure was harsh, some of the counts (TCA and methanol washes) were likely biomass components (amino acids, etc.) removed from lysed cells.

As shown in Table 2, 2 percent (culture A1) and 6 percent (culture A2) of the $^{14}$C-TNT ring carbons were recovered as $^{14}CO_2$ and 4 percent (culture A1) and 5 percent (culture A2) as $^{14}$C-volatile compounds after 24 hours. Also, at least 2 percent of the label became incorporated into cellular biomass. When combined with the data on viable plate counts, these total recoveries of 9 to 13 percent of the $^{14}$C as $CO_2$, volatile compounds, and/or biomass carbon indicate that TNT is degraded and mineralized by LJP-1 within a 24-hour period, particularly since the control produced no $^{14}CO_2$ $^{14}$C-volatiles, or $^{14}$C-biomass (in the control, essentially all the recoverable counts resided in the culture medium).

Table 2 also shows that, in all the cultures, most of the counts were recovered in the spent culture medium as soluble radioactivity. Thus, the distribution of counts as TNT and/or intermediates of TNT degradation were investigated. HPLC analyses of the control indicated that, after 24 hours, most counts (79 percent of the total soluble counts) appeared as 4-amino-2,6-dinitrotoluene (4A26DNT). This indicated that essentially total abiotic chemical reduction of the 4-nitro group of TNT had occurred in the control, probably due to the highly reducing conditions present in this medium (no TNT was detected by HPLC). Nine percent of the total soluble counts were present as 2,4-diamino-6-nitrotoluene (24DA6NT), and the remaining soluble counts were present as an unknown compound having a 3.04-minute retention time.

In culture A1, no radioactivity as TNT was detected in the supernatant. The amount of 4A26DNT, representing about 22 percent of the total soluble radioactivity, was reduced about 75% relative to the control. No significant amount of 24DA6NT was detected, although a small amount of radioactivity (3 percent of the total soluble radioactivity) was detected in HPLC fractions having a similar retention time. Most of the radioactivity (75 percent of the total soluble counts) was found in the void volume.

No TNT was detected in the supernatants from culture A2. The amount of 4A26DNT, representing about 24 percent of the total soluble radioactivity, was reduced about 81 percent compared to the control. No 24DA6NT was detected. Whereas no peaks were detected by HPLC at retention times between 7-8 minutes, some radioactivity (6 percent of the total soluble counts) was present in fractions corresponding to this retention time.

As in culture A1, most of the soluble radioactivity (70 percent) of culture A2 eluted from the HPLC column with the void volume. The specific identities of compounds in the void volume have not been determined, but they are aliphatic compounds.

The foregoing results indicate that substantial TNT degradation, followed by removal of TNT degradation intermediates, occurred in the inoculated cultures (A1 and A2).

To further characterize the microorganisms comprising the LJP-1 culture, a loop of cells from a stock slant of the LJP-1 culture was inoculated into anaerobic Peptone-Pepticase-Yeast Extract (PPY) broth in a 50-mL flask and incubated anaerobically, without shaking at room temperature until turbid (24 hr). Cells from this culture were then streaked onto PPY agar to isolate individual colonies.

An isolate was isolated anaerobically from a culture slant of LJP-1 by heat-shocking the slant at 65° C. for 20 minutes, and then streaking the surviving cells onto solid PPYA medium. The isolate, obtained from a single colony, comprised rod-shaped bacteria (about 2.7 µm×1.1 µm) growing in chains of up to four cells. The bacteria produced ellipsoidal spores that did not swell the sporangia. According to results of API AN-IDENT tests and evaluation of other morphological characteristics of LJP-1, this isolate was classified as a strain of Clostridium bifermentans.

In sum, LJP-1 has been shown to degrade TNT to $CO_2$ and organic acids. LJP-1 can use TNT as a carbon and nitrogen source and is able to fix atmospheric $CO_2$. LJP-1, an obligate anaerobe, was determined to be a strain of Clostridium bifermentans capable of forming heat-resistant endospores. TNT degradation using LJP-1 is best performed at about 30° C. with some carbon and/or amino-acid supplementation (but such supplementation is not required). Particularly in the presence of yeast extract, TNT degradation can occur in as little as 24 hours. LJP-1 can be used to remove TNT and nitramines such as RMX and HMX from soil or water contaminated with one or more of such compounds.

The LJP-1 isolate has been deposited with the American Type Culture Collection (ATCC) under accession number ATCC 55559.

V. Degradation of TNT in Munitions-Contaminated Soil Using Isolated Clostridium Co-cultures An anaerobic consortium was established in a chemostat using procedures as described above. The microorganisms were cultured in a medium containing essential nutrients. Over time, the culture was supplemented with TNT as a sole carbon source.

After the consortium had become adapted to degrade the TNT, a sample from the chemostat was streaked onto plates of agar, including mineral salts, as described above, and 100 ppm TNT. The streaked sample grew as a mixture of white and clear colonies each consisting of gram-positive, strictly anaerobic bacteria that produce heat-resistant endospores. The bacteria seem to be of two morphologies: one type exhibiting classical Clostridium rod-shaped morphology and the other type exhibiting clostridial coccoid morphology. Both were designated as Clostridium species. The bacteria in each white or clear colony appeared to be of both morphologies; thus, both the white and clear colonies were termed "co-cultures."

Cultures obtained from stocks derived from either the white or clear colonies were found to degrade TNT similarly. Working with bacteria from a white colony, the two cell types have been isolated from each other.

To examine TNT degradation by the co-cultures, standard anaerobic techniques and anaerobic serum bottles were used. Cells were maintained in a rich liquid medium, TSB plus 0.3% yeast extract, and subcultured every week. For degradation experiments, WR-86 minimal medium (ph 7.3) was used with or without 3 % (w/w) added starch. TNT, when present, was added at 100 ppm. A 10-percent (v/v) inoculum was used in all experiments, and cultures were incubated at 32° C. A vitamin-B supplement was used in all samples. In some experiments, TNT-contaminated soil was used in place of pure TNT. TNT-contaminated soil (0.33 g in 40 mL of medium) was added to form a slurry, thereby yielding a final concentration of 100 ppm TNT. Residual TNT and the appearance and disappearance of TNT degradation intermediates were monitored by HPLC. All data were calculated averages of samples taken from duplicate anaerobic serum bottles.

Experiments were set up using a set of nine treatments, as listed in Table 3. Co-cultures from the white and clear colonies were examined separately, and in each instance were examined for the presence or absence of a co-substrate (3% w/v starch). Two controls were included. In one control (Sample B), the bacteria were inactivated by addition of 10% w/v formaldehyde to check the cultures for abiotic transformations of TNT under the highly reducing conditions of the anaerobic incubations. In another control (Sample A), the soil added thereto was sterilized by autoclaving (all other samples included non-sterile soil) to examine whether TNT biodegradation could be mediated by enrichment of the natural microflora of the soil, or whether inoculation with the TNT-degrading Clostridium culture isolated above was required for TNT degradation. Samples C' and D' represent replications of Samples C and D, respectively, wherein the white colony cultures were grown on TNT in the presence of starch.

TABLE 3

| Sample | 10% inoculum | Carbon Source | 10% Formald |
|---|---|---|---|
| A | none | 3% starch | no |
| B | white colonies | 3% starch | added |
| C | white colonies | none | no |
| D | white colonies | none | no |
| E | none | 3% starch | no |
| F | clear colonies | none | no |
| G | clear colonies | 3% starch | no |
| C' | white colonies | 3% starch | no |
| D' | white colonies | 3% starch | no |

Figure 3:
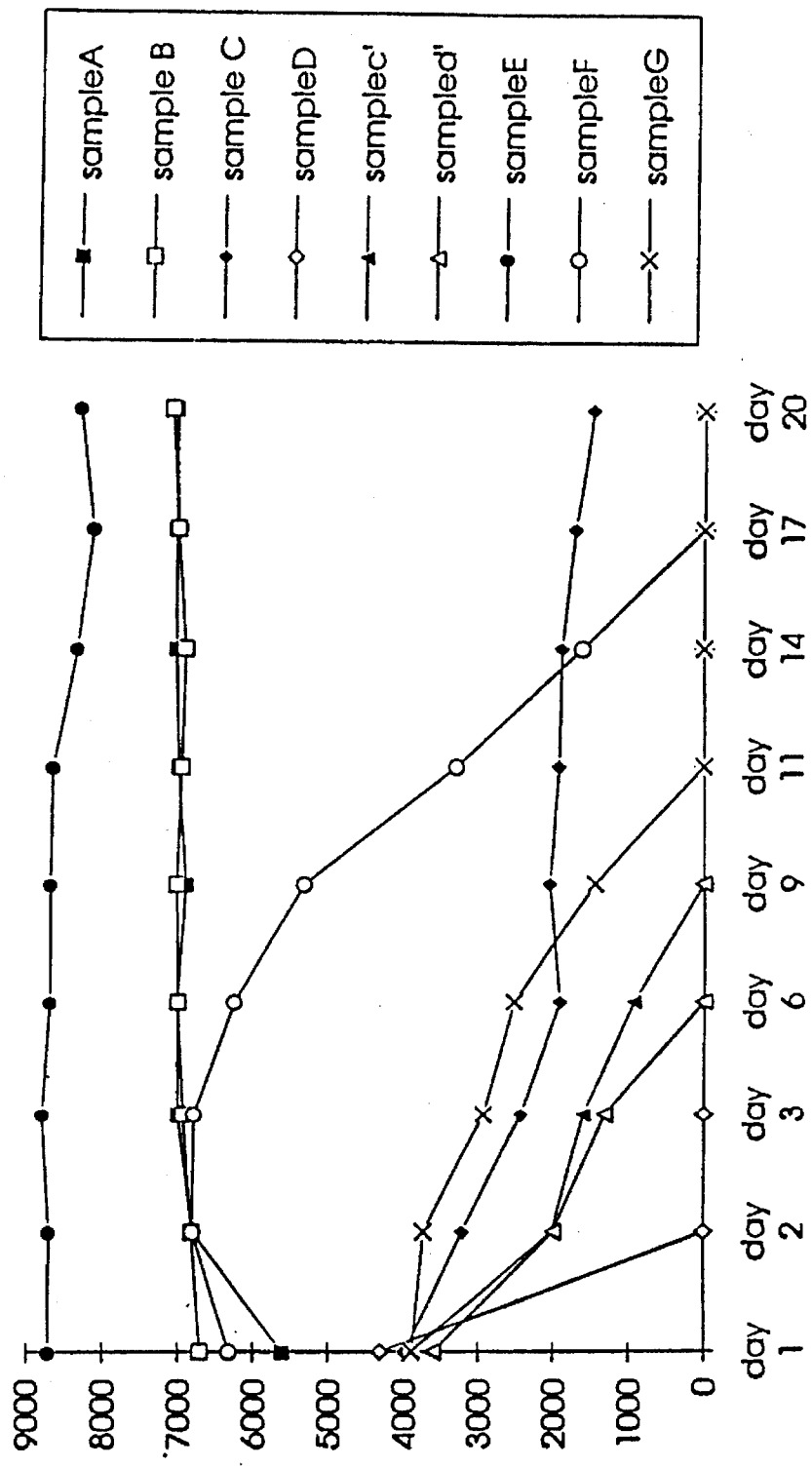
FIG. 3 shows the results of experiments investigating TNT degradation by bacterial isolates, including the LJP-1 strain according to the present invention, compared to the TNT-degrading ability of autoclaved soil (Sample A), soil containing formaldehyde-killed microorganisms (Sample B), a microorganism culture lacking TNT-degrading microorganisms (Sample E), and other TNT-degrading isolates (Samples C, D, C', D', F and G)

FIG. 3 shows the experimental results using the samples in Table 3 (wherein the units of the ordinate are units of concentration as determined using an HPLC). The autoclaved, uninoculated soil (Sample A) and the formaldehyde-killed uninoculated soil (Sample B) showed no TNT degradation. Neither did the non-sterile TNT-contaminated soil (containing indigenous microorganisms), even with starch present (Sample E). Thus, the non-sterile soil did not contain a microflora that could be immediately used to degrade the TNT. But, when the microbiological population of the non-sterile soil was augmented with either the white or clear clostridial co-cultures (Samples C, D, C', D', F, and G), TNT degradation was observed, wherein TNT degradation was generally more rapid in the presence of added starch. (In another experiment, it was found that a 10% clostridial inoculum containing 3% w/v starch exhibited complete removal of 100 ppm TNT from soil in 24 hours at room temperature.) Transient intermediates arising as a result of TNT degradation included 4-amino-2,6-dinitrotoluene (4A-2,6-DNT) and 2,4-diamino-6-nitrotoluene (2,4-DA-6-NT). These intermediates accumulate during early stages of TNT degradation, but then are themselves degraded.

Thus, both clostridial co-cultures are capable of bioremediating a soil containing 100 ppm of TNT.

VI. Isolation of a Third Bacterial Strain (KMR-1) Capable of Degrading Nitroaromatics and Nitramines An anaerobic consortium was initially established in a chemostat as described above. From the consortium, a bacterial isolate was obtained that is capable of degrading RDX and other nitramines.

For this work, all bacterial manipulations and media preparations were performed anaerobically. Brain heart infusion (BHI) broth containing 30 ppm RDX was inoculated with a sample (1 mL) of the anaerobic consortium and incubated anaerobically overnight at 37° C. Samples from the overnight incubation were streaked onto BHI agar plates (lacking any nitroaromatic or nitramine compounds) and incubated anaerobically at 37° C. Colonies that appeared were isolated and purified.

Isolates that appeared dissimilar from one another were picked from the BHI agar plates and stored on anaerobic BHI agar slants. Nine isolates were selected for evaluation testing of a possible ability to degrade RDX. One strain, designated KMR-1, when cultured for 72 hours in the presence of RDX, exhibited the best reduction of RDX concentration in the culture medium of all the isolates tested, and was investigated further.

Using the API anaerobe identification system, KMR-1 was identified as a strain of Clostridium bifermentans, which is a motile, urease-negative, gram-positive, obligate anaerobic bacillus that forms endospores.

In an experiment to determine how resilient the spores of C. bifermentans are to oxygen exposure, pure oxygen was sparged for various lengths of time through nutrient medium supplemented with 50 ppm TNT and containing an active culture of the bacterium. It was thus found that oxygen is toxic to these bacteria since viable colony counts dropped, upon exposure to oxygen for 18 hours, from $1\times10^8$ cfu/mL to $1\times10^5$ cfu/mL. However, further exposure of the culture to oxygen resulted in no further decrease in viability, presumably because the surviving cells were able to form spores that were oxygen insensitive. This was an important finding indicating that the viability of the various isolated Clostridium bifermentans strains according to the present invention to a large-scale bioremediation project would likely suffer no adverse effects from an initial aerobic stage.

Figure 4:
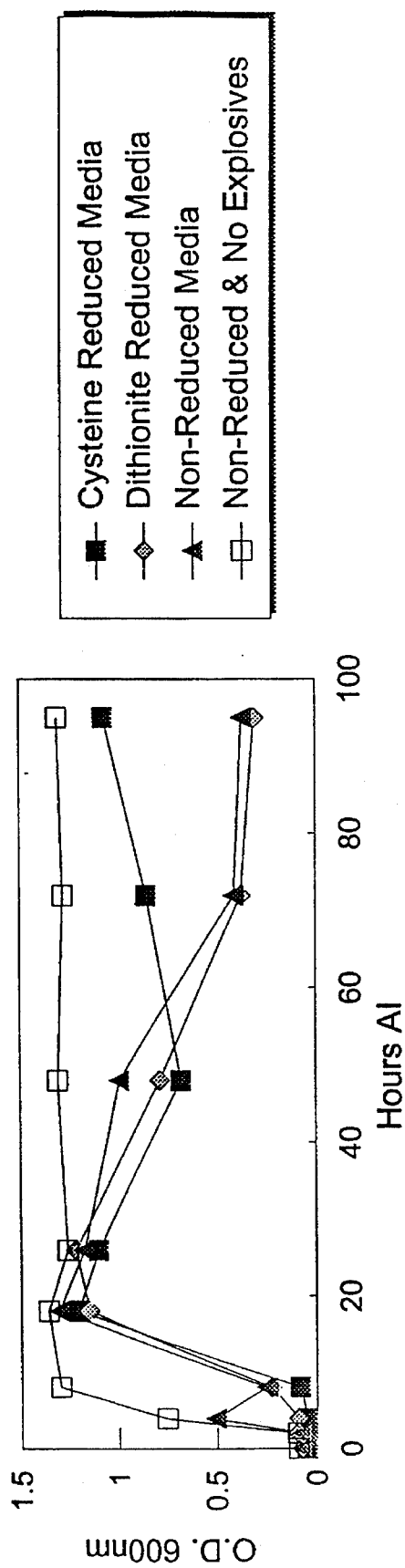
FIG. 4 is a plot showing results of an experiment investigating the ability of the KMR-1 strain, according to the present invention, to grow in the presence or absence of nitroaromatics and nitramines ("explosives") and in the presence or absence of a reductant such as cysteine or dithionite.

The growth of strain KMR-1 was monitored by optical density (OD) at 600 nm in the presence of various nitroaromatics and nitramines (i.e., "explosives") and various reductants (e.g., cysteine or dithionite which serve as oxygen scavengers). The results are shown in FIG. 4. Over a period of 100 hours, KMR-1 was observed to grow to a high OD in non-reduced medium containing no nitroaromatics or nitramines (i.e., "no explosives"); this OD was higher than that attained by KMR-1 on medium containing explosives and either a reductant or no reductant. Growth of KMR-1 in medium containing explosives exhibited a significant time lag, regardless of whether a reductant was present or not.

Figure 5:
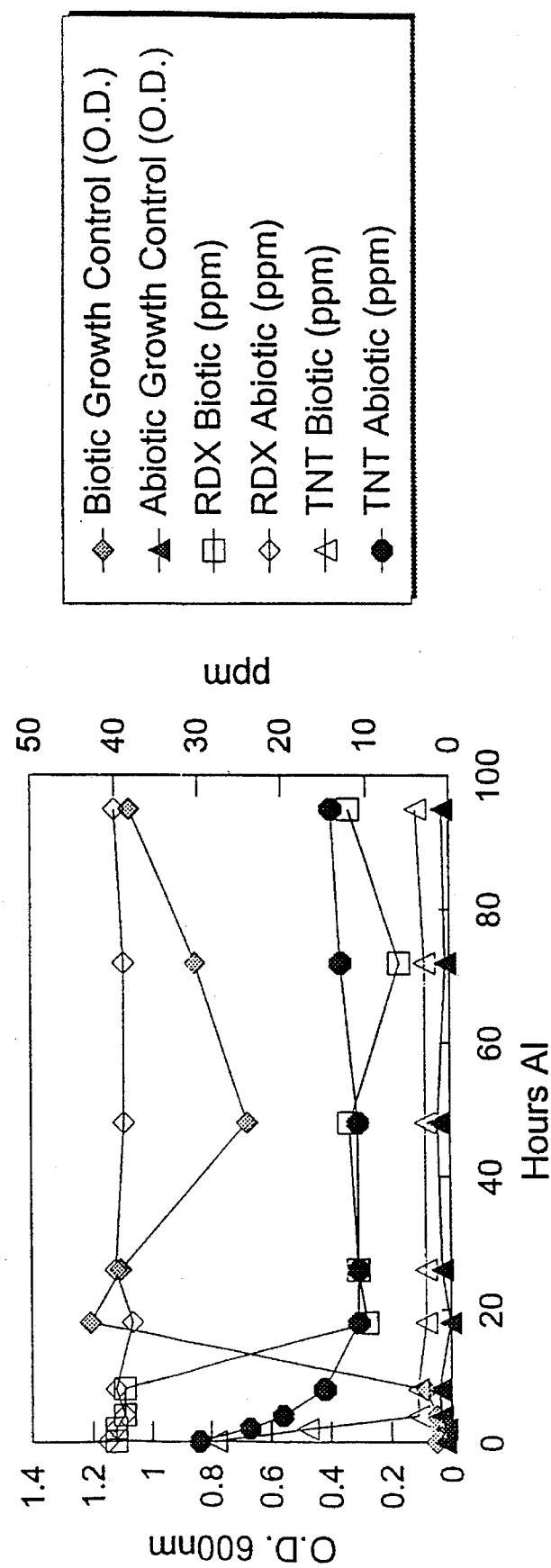
FIG. 5 is a plot of the results of an experiment investigating the growth (measured by optical density) of strain KMR-1 after inoculation ("AI") in a reductant (cysteine)-containing medium having $E_h$=−210 mV and including either TNT or RDX.
Figure 6:
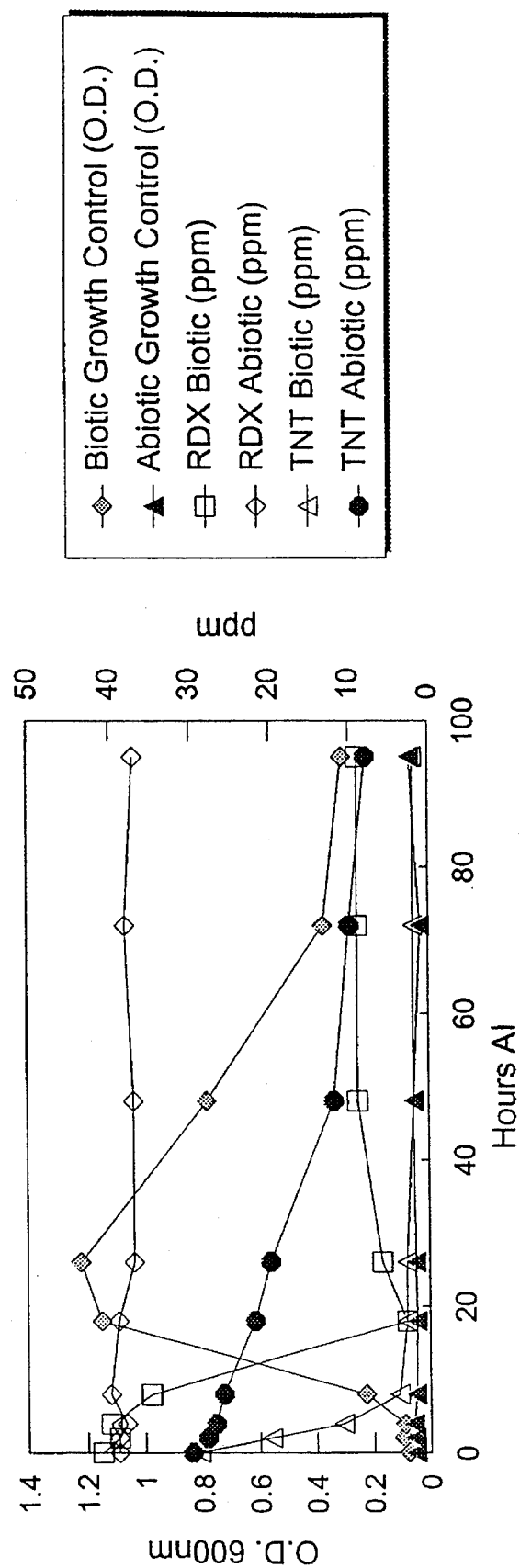
FIG. 6 is a plot of the results of an experiment similar to that shown in FIG. 5 except that the medium contained dithionite as a reductant and $E_h$<−600 mV.
Figure 7:
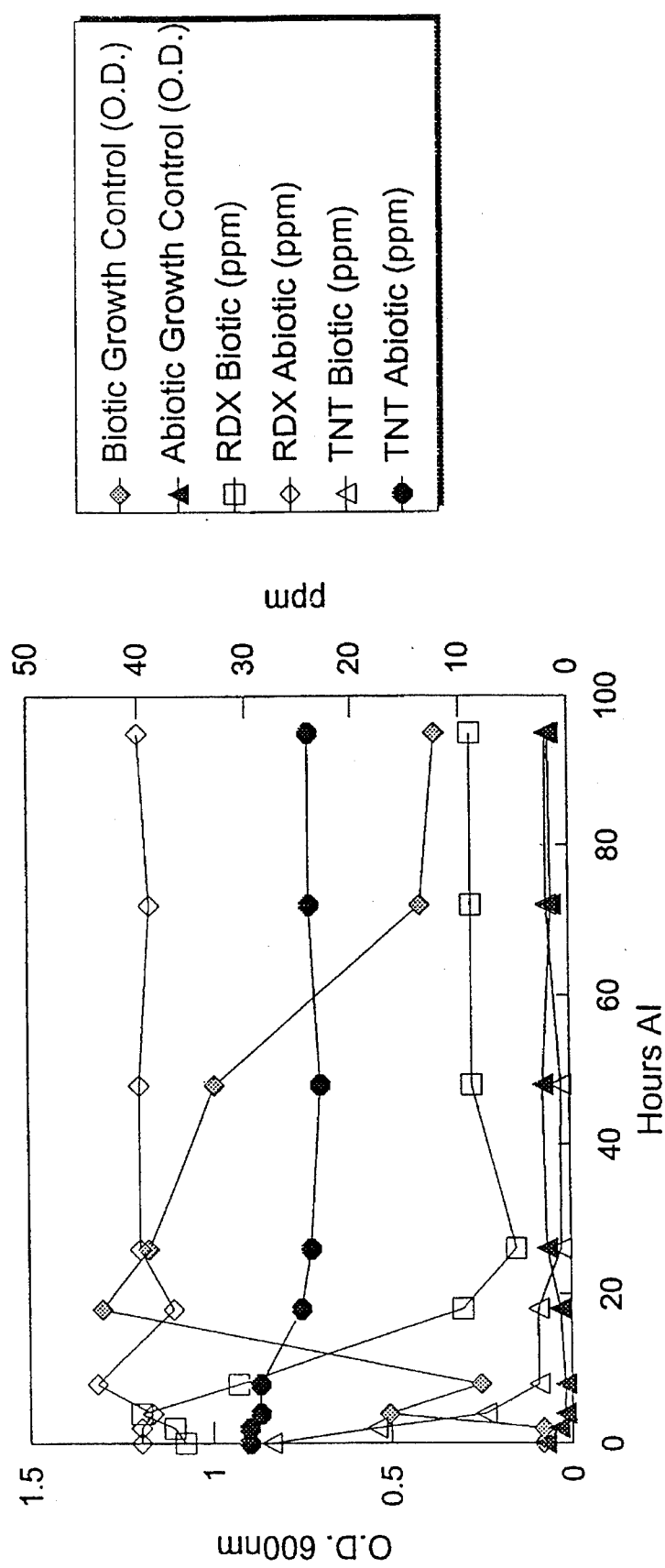
FIG. 7 is a plot of the results of an experiment similar to that shown in FIG. 5 except that the medium lacked a reductant ($E_h$ not determined).

FIGS. 5–7 depict the results of KMR-1 growth experiments in which the KMR-1 strain was cultured for various times (hours after inoculation (abbreviated "AI")) in reduced or non-reduced BHI medium containing either RDX or TNT explosives. In FIG. 5, the medium is reduced using cysteine, yielding a redox potential (Eh) of about −210 mV. In FIG. 6, the medium is reduced using dithionite, yielding an $E_h$ value of less than −600 mV. In FIG. 7, the medium is not reduced ($E_h$ not determined). In all three experiments, co-metabolism of TNT, resulting in degradation of TNT, occurred prior to co-metabolism of RDX. Cell numbers did not increase until TNT concentrations approached minimal levels. After the TNT concentrations dropped, cell counts increased with concurrent co-metabolism of RDX. Only after the RDX concentrations reached a minimum did the cell counts in the cultures reach maximum levels.

In the abiotic controls (i.e., sterile cultures), RDX concentrations did not decrease in any of the reducing media, but TNT concentrations did undergo some decrease; the more reduced the medium, the greater the decrease in TNT concentration under abiotic conditions. Nevertheless, in all three experiments, the decrease in explosive concentration was substantially greater under biotic conditions than under abiotic conditions.

In similar experiments (data not shown), KMR-1 also exhibited an ability to degrade the nitroaromatic dinoseb.

Strain KMR-1 has ATCC accession number ATCC 55560.

VII. Representative Methods for Degradation of Nitroaromatic- and/or Nitramine-contaminated Soil or Water Using the Isolates The isolates according to the present invention, as discussed above, can be used in methods as set forth in detail in U.S. patent application Ser. No. 08/096,735, incorporated herein by reference. In that reference, methods are disclosed that are applicable for degrading contaminant nitroaromatics in water or soil. In the case of soil, sufficient water is added to the soil to produce a "fluid medium" (i.e., a slurry of the soil). Before biodegradation can begin, the fluid medium is rendered rapidly anaerobic preferably by adding a carbohydrate (such as starch) and an inoculum of fermentative aerobic microorganisms. The aerobic microorganisms rapidly metabolize a portion of the starch while thereby rapidly consuming oxygen in the medium. As a result, the redox potential of the fluid medium is rapidly lowered to strictly anaerobic levels (about −200 mV or less). An inoculum comprising a consortium of anaerobic microorganisms is then added to the fluid medium. The anaerobic consortium is specially adapted to degrade the contaminant nitroaromatic in the fluid medium. Such an anaerobic consortium can be prepared, for example, by using a chemostat as described above or can be obtained from a fluid medium that had been previously remediated according to the method disclosed in that reference.

An anaerobic isolate according to the present invention can be used in a method as described in the preceding paragraph for degrading a contaminant nitroaromatic and/or nitramine compound in the fluid medium. Instead of adding an inoculum of the anaerobic consortium to the fluid medium, an inoculum of said isolate is added instead. It is not necessary to establish in the fluid medium a pure culture of the anaerobic isolate (i.e., the fluid medium need not be sterile before adding the isolate); rather, the inoculum of the isolate simply augments the resident population of microorganisms sufficiently to achieve degradation of the contaminant nitroaromatic and/or nitramine in the medium.

Other protocols can be used to render the fluid medium anaerobic besides employing an initial aerobic phase. However, in large-scale operations of methods according to the present invention and/or in operations conducted in the field, a preliminary aerobic phase is usually the most practical and/or economical. Other protocols that can be used under certain conditions include heating the fluid medium sufficiently to drive off most of the residual oxygen, followed by addition of an amount of a reductant (oxygen scavenger) sufficient to substantially scavenge the remaining oxygen so as to lower the redox potential to a level of about −200 mV or less. Alternatively, an inert gas can be passed through the fluid medium to purge substantially all the absorbed oxygen from the medium. It will be appreciated that other protocols, either existing or yet to be invented, may also be applicable for reducing the redox potential of the fluid medium to a level of about −200 mV or less; i.e., how the medium is rendered sufficiently anaerobic for degradative activity by the isolate is of no consequence, so long as anaerobiosis is achieved.

Particularly in methods according to the present invention that do not include an initial aerobic phase (which would require the addition to the fluid medium of a rapidly metabolizable carbon and energy source such as starch), degradation of contaminant nitroaromatics and/or nitramines by an anaerobic isolate according to the present invention is facilitated by providing an extraneous carbon and energy source to the anaerobic microorganisms. The extraneous carbon and energy source can comprise starch or any of various sugars such as glucose. Starch is more slowly metabolized than free sugar. Also, starch may be more conveniently employed in large operations. Smaller operations can be satisfactorily performed using a free sugar, preferably glucose. The rapid metabolism of free sugars by these microorganisms is not a problem (particularly when degrading nitroaromatics such as TNT) because, as disclosed above, degradation reactions are surprisingly rapid and frequently occur before the available supply of sugar is exhausted.

As discussed above, the general pH range for methods according to the present invention is about 6 to 8, with a preferred range of about 6.5 to 7. In methods according to the present invention, pH within this range can be established and maintained using a buffer such as a phosphate buffer (concentration about 50 mM).

For degrading TNT and RDX in contaminated soils, a ratio of soil to liquid of about 1 percent can be too low for large-scale operations. The rate at which TNT dissociates from soil particles and enters the aqueous phase of a fluid medium is governed mostly by solubilization rather than desorption. This suggests that TNT is not adsorbed onto soil particles but rather is present as a solid in the soil matrix. Increasing the soil concentration to about 4% relative to the liquid increases the amount of TNT initially in the liquid to the apparent solubility limit of TNT in the liquid.

The isolates according to the present invention are particularly adept at degrading nitroaromatics and nitramines to organic acids such as acetate. Complete mineralization of the acetate to carbon dioxide is readily accomplished by the action of other anaerobes present in the fluid medium which co-metabolize the organic acids. This mineralization can also be performed under aerobic conditions. Thus, in methods according to the present invention in which the only anaerobic microorganisms present in the fluid medium are of an isolate according to the present invention, an aerobic stage can be employed after the anaerobic stage (and the contaminant nitroaromatics and/or nitramines have been degraded to organic acids) for achieving mineralization of the organic acids and to consume other fermentation products that may have accumulated during the anaerobic stage.

Having illustrated and described the principles of our invention with reference to detailed descriptions of process steps and specific examples, it should be apparent to those of ordinary skill in the art that the invention may be modified in arrangement and detail without departing from such principles. We claim as our invention all such modifications as come within the true spirit and scope of the following claims.

We claim:

1. A biologically pure culture of strain LJP-1 of Clostridium bifermentans, having all identifying characteristics of said strain deposited under accession number ATCC 55559.

2. A strain as recited in claim 1 capable of degrading nitroaromatics and nitramines.

3. An inoculum comprising a strain as recited in claim 1 in a physiologically compatible carrier.

4. A biologically pure culture of strain SBF-1 of Clostridium bifermentans, having all identifying characteristics of said strain deposited under accession number ATCC 55561.

5. A strain as recited in claim 4 capable of degrading nitroaromatics and nitramines.

6. An inoculum comprising a strain as recited in claim 4 in a physiologically compatible carrier.

7. A biologically pure culture of strain KMR-1 of Clostridium bifermentans, having all identifying characteristics of said strain deposited under accession number ATCC 55560.

8. A strain as recited in claim 7 capable of degrading nitroaromatics and nitramines.

9. An inoculum comprising a strain as recited in claim 7 in a physiologically compatible carrier.

10. A method for degrading molecules of a nitroaromatic or nitramine compound present as a contaminant in a fluid medium to reduce the concentration of the nitroaromatic or nitramine compound in the fluid medium, the method comprising:

(a) reducing the redox potential of the fluid medium to a level of about −200 mV or less so as to render the fluid medium anaerobic;

(b) adding to the fluid medium an inoculum comprising anaerobic microorganisms, the anaerobic microorganisms being selected from a group consisting of strains SBF-1, LJP-1, and KMR-1, and mixtures thereof, said strains having all identifying characteristics Of microorganisms deposited under accession numbers ATCC 55559, ATCC 55561, and ATCC 55560, respectively; and (c) maintaining anaerobic conditions in the fluid medium for a time sufficient for the anaerobic microorganisms to degrade the contaminant nitroaromatic or nitramine compound.

11. A method as recited in claim 10 including the step of adding to the fluid medium a carbohydrate that can be utilized as a carbon and energy source by the anaerobic microorganisms.

12. A method as recited in claim 10 including the step of maintaining the fluid medium at a pH of 6 to 8 while maintaining the anaerobic conditions in the fluid medium.

13. A method as recited in claim 10 including the step of maintaining the temperature of the fluid medium within a range of 15 to 37° C.

* * * * *

UNITED STATES PATENT AND TRADEMARK OFFICE
CERTIFICATE OF CORRECTION

PATENT NO. : 5,455,173
DATED : October 3, 1995
INVENTOR(S) : Crawford et al.

It is certified that error appears in the above-identified patent and that said Letters Patent is hereby corrected as shown below:

On the Cover Page:
Second column, under the heading "[56] References Cited, Other Publications," "Goszcynski" should be --Goszczynski--.

Second column, under the heading "[56] References Cited, Other Publications," "[phenyl-u-$^{14}$C]" should be --[phenyl-U-$^{14}$C]--.

Page 2, first column, under the heading "[56] References Cited, Other Publications," delete "(1994)" as the year of publication of the Channon et al. reference and in lieu thereof insert --(1944)--.

Title page item [57],
In the Abstract:
On line 13 of the abstract, "<- 200 mV" should be --$\leq$ -200 mV--.

Column 1, lines 11-12, "U.S. Pat. No. 5,787,271," should be --U.S. Pat. No. 5,387,271,--.

Column 4, line 37, "$E_h$_.210 mV" should be --$E_h$ = -210 mV--.

Column 4, line 41, "$E_h$<.600 mV" should be --$E_h$ < -600 mV--.

Column 5, line 3, "$MgSO_4.7H_2O$" should be --$MgSO_4 \cdot 7H_2O$--.

Column 5, line 3, "$CaCl_2.2H_2O$" should be --$CaCl_2 \cdot 2H_2O$--.

Column 5, line 52, "$MnCl_2.4H_2O$" should be --$MnCl_2 \cdot 4H_2O$--.

UNITED STATES PATENT AND TRADEMARK OFFICE
CERTIFICATE OF CORRECTION

PATENT NO. : 5,455,173
DATED : October 3, 1995
INVENTOR(S) : Crawford et al.

It is certified that error appears in the above-identified patent and that said Letters Patent is hereby corrected as shown below:

Column 5, line 53, "$Na_2MoO_4.2H_2O$" should be --$Na_2MoO_4 \cdot 2H_2O$--.

Column 5, line 54, "$CoCl_1.6H_2O$" should be --$CoCl_2 \cdot 6H_2O$--.

Column 5, line 54, "$NiCl_2.6H_2O$" should be --$NiCl_2 \cdot 6H_2O$--.

Column 6, line 11, "$NaS_2O_4.2H_2O$" should be --$NaS_2O_4 \cdot 2H_2O$--.

Column 14, line 63, "(Eh)" should be --($E_h$)--.

Column 18, line 9, "characteristics Of" should be --characteristics of--.

Signed and Sealed this

Twenty-first Day of October 1997

Attest:

BRUCE LEHMAN

*Attesting Officer*    *Commissioner of Patents and Trademarks*